(12) United States Patent
Mehra et al.

(10) Patent No.: US 10,842,896 B1
(45) Date of Patent: Nov. 24, 2020

(54) DEVICE FOR DISINFECTING A PORTABLE OBJECT

(71) Applicant: Tech Goods USA Inc., Sugar Land, TX (US)

(72) Inventors: Anuj Mehra, Sugar Land, TX (US); Sanandan Sudhir, Delhi (IN)

(73) Assignee: Tech Goods USA Inc., Sugar Land, TX (US)

( * ) Notice: Subject to any disclaimer, the term of this patent is extended or adjusted under 35 U.S.C. 154(b) by 0 days.

(21) Appl. No.: 16/884,926

(22) Filed: May 27, 2020

Related U.S. Application Data

(60) Provisional application No. 63/000,920, filed on Mar. 27, 2020.

(51) Int. Cl.
*G01N 23/00* (2006.01)
*A61N 5/00* (2006.01)
(Continued)

(52) U.S. Cl.
CPC ........ *A61L 2/10* (2013.01); *A61L 2/22* (2013.01); *A61L 2/24* (2013.01); *G05B 15/02* (2013.01);
(Continued)

(58) Field of Classification Search
CPC .............. A61L 2/10; A61L 2/22; A61L 2/24; G05B 15/02; H02J 7/025; B60N 3/14
(Continued)

(56) References Cited

U.S. PATENT DOCUMENTS

| | | | | |
|---|---|---|---|---|
| 2,235,296 | A | * | 3/1941 | Muncheryan ............. A61L 2/10 250/455.11 |
| 2,253,250 | A | * | 8/1941 | Selig ........................ A61L 2/10 250/455.11 |

(Continued)

FOREIGN PATENT DOCUMENTS

| | | |
|---|---|---|
| CN | 1170294 A | 1/1998 |
| CN | 105209181 A | 12/2015 |

(Continued)

OTHER PUBLICATIONS

Search Report and Written Opinion dated Aug. 10, 2020 for co-pending related PCT App. No. PCT/US20/34734.

*Primary Examiner* — Monzer R Chorbaji
(74) *Attorney, Agent, or Firm* — D'Ambrosio & Menon, PLLC; Usha Menon

(57) ABSTRACT

A device for disinfecting a portable object comprising: a housing comprising an outlet, and wherein the housing encloses a central cavity; a first panel located on an upper surface of the housing, the first panel configured to move between an open and a closed position, wherein in a closed position, the panel is configured to receive the portable object, and wherein in an open position, the object is configured to be moved into the cavity; a first platform configured inside the cavity, the first platform configured to move the object between a first position and a second position inside the cavity; and a plurality of ultraviolet (UV) lights positioned over an upper surface of the first platform and along inner sidewalls of the housing cavity, wherein the UV lights are configured to emit UV light of a predetermined wavelength to disinfect the object. The disinfected object is transferred to a conveyor which moves the object towards the outlet. The device can include a heating unit over the conveyor for controlled heating of the disinfected object. The device can also include a sanitizer sprayer (Continued)

positioned between the heating unit, to spray an aromatic sanitizer on the object before it exits the device.

16 Claims, 10 Drawing Sheets

(51) Int. Cl.
```
A61L 2/10      (2006.01)
G05B 15/02     (2006.01)
G06Q 20/14     (2012.01)
A61L 2/24      (2006.01)
A61L 2/22      (2006.01)
G06Q 20/02     (2012.01)
```

(52) U.S. Cl.
CPC .......... *G06Q 20/027* (2013.01); *G06Q 20/14* (2013.01); *A61L 2202/11* (2013.01); *A61L 2202/121* (2013.01); *A61L 2202/122* (2013.01); *A61L 2202/14* (2013.01); *A61L 2202/15* (2013.01)

(58) Field of Classification Search
USPC ...... 422/22, 24; 250/455.11, 453.11, 454.11, 250/492.1, 494.1, 504 R; 361/807
See application file for complete search history.

(56) References Cited

U.S. PATENT DOCUMENTS

| | | | |
|---|---|---|---|
| 6,560,335 B2 | 5/2003 | Zohn et al. | |
| 7,507,369 B2 * | 3/2009 | Lu | A61L 2/04 219/679 |
| 7,513,193 B2 * | 4/2009 | Allen | A01C 1/08 250/433 |
| 8,337,770 B2 * | 12/2012 | Wind | A61L 2/10 422/186.3 |
| 8,689,461 B1 | 4/2014 | Cookson | |
| 8,964,405 B2 | 2/2015 | La Porte | |
| 9,265,849 B2 | 2/2016 | Kerr | |
| 9,339,567 B2 | 5/2016 | LaPorte et al. | |
| 9,392,853 B2 | 7/2016 | Lawler | |
| 9,460,309 B2 | 10/2016 | Zar | |
| 9,522,201 B2 | 12/2016 | Sunkara et al. | |
| 9,583,968 B2 | 2/2017 | Salter | |
| 2005/0056596 A1 * | 3/2005 | Paskalov | C02F 1/005 210/748.01 |
| 2014/0353201 A1 | 12/2014 | Molineux | |
| 2016/0074546 A1 * | 3/2016 | Rizzone | A61L 2/26 250/455.11 |
| 2018/0117192 A1 * | 5/2018 | Baranov | A61L 2/08 |
| 2019/0107238 A1 | 4/2019 | Molineux | |

FOREIGN PATENT DOCUMENTS

| | | |
|---|---|---|
| CN | 107971263 A | 5/2018 |
| CN | 108067449 A | 5/2018 |
| CN | 209075551 U | 7/2019 |
| EP | 2852302 A1 | 4/2015 |
| KR | 101367256 B1 | 2/2014 |
| KR | 20140041040 A | 4/2014 |
| KR | 20140061594 A | 5/2014 |
| KR | 20170107801 A | 9/2017 |

* cited by examiner

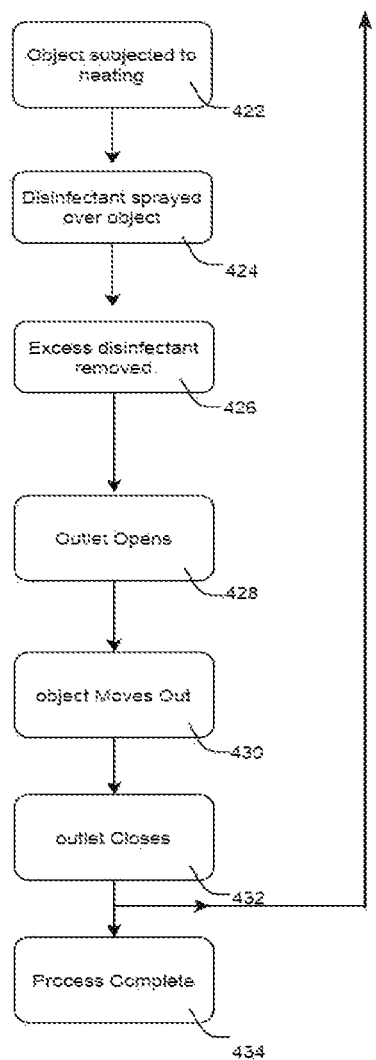
FIG 4A (Contd.)

DEVICE FOR DISINFECTING A PORTABLE OBJECT

CROSS-REFERENCE TO RELATED APPLICATION

This application claims priority from U.S. Provisional Patent Application No. 63/000,920 filed on Mar. 27, 2020, entitled "SYSTEMS AND METHODS FOR DISINFECTING PORTABLE OBJECTS", the entire disclosure of which is part of the disclosure of the present application and is hereby incorporated by reference in its entirety.

TECHNICAL FIELD

The present disclosure relates to the field of disinfecting devices. More particularly, the present disclosure relates to a compact, efficient and easily operable device for disinfecting a portable object, such as, a mobile phone.

BACKGROUND

The background description includes information that may be useful in understanding the present invention. It is not an admission that any of the information provided herein is prior art or relevant to the presently claimed invention, or that any publication specifically or implicitly referenced is prior art.

Diseases caused due to microorganisms mainly spread during close contact and by small droplets produced when an infected person coughs, sneezes or talks. These droplets may also be produced during breathing and speaking. People may also become infected by the microorganisms by touching a contaminated surface and then their face or eyes.

Coronaviruses are a group of related viruses that cause diseases in mammals. In humans, coronaviruses cause respiratory tract infections that can range from mild to lethal. Mild illnesses include some cases of the common cold (which has other possible causes, predominantly rhinoviruses), while more lethal varieties can cause SARS, MERS, and COVID-19.

Infections due to bacteria and viruses commonly spread through daily used objects. Some of these objects, like portable electronic devices are a ubiquitous part of life. Bacteria and viruses can survive on the surfaces of these daily used objects for a much longer time. The electronic devices, such as, mobile phones, are routinely exposed to germs and microorganisms. For example, viruses and germs are transferred from the user's hands to their mobile phones. Scientists have found that mobile phones can carry ten times more bacteria than most restrooms. In addition, according to various scientific reports, viruses such as COVID-19 can rest up to 72 hours on certain objects and surfaces.

Various disinfecting products are currently available. However, such disinfecting products are not available to users everywhere. Further, even if the disinfecting products are available to the user, they fail to efficiently disinfect overall surface of the objects.

There is, therefore, a need to provide a portable and easily operable device for disinfecting and sterilizing objects. The device should be safe to use and should be able to efficiently disinfect the entire surface of an object.

SUMMARY

The present disclosure relates to the field of disinfecting objects. The terms sterilizing, sanitizing and disinfecting are used interchangeably herein to mean the destruction of microorganisms, such as, viruses and bacteria. More particularly, the present disclosure relates to a compact, efficient and easily operable device for disinfecting a portable object. The device is configured to be easily installed at various locations.

According to an embodiment, a device for the disinfection of a portable object is provided. The portable object ("object") can include, without limitation, electronic devices, such as, a cell/mobile phone, a smartphone, a tablet computer and any palmtop computing device. In another embodiment, the object can include a face mask, household objects, jewellery, medical equipment, such as, forceps, and any other equipment that need to be sterilized prior to use/re-use. The device can be configured to efficiently disinfect an overall surface area of the object.

In an embodiment, the device comprises UV lights for disinfecting the object. The device can further include means for providing a gentle heat to further disinfect the object. The device can also be configured to spray a cleanser/sanitizer on the object. The sanitizer can be an aromatic sanitizer.

The device can be placed in a high traffic area, such as, at a retail store, an airport terminal, a mall, a hospital, a restaurant, a hotel, a school, and an office building. The device can also be configured for home use and/or use in any desired private or public place. The device can be configured to be easily operated by users.

According to an embodiment, the device for disinfecting a portable object comprises: a housing comprising an outlet, wherein the housing encloses a central cavity; a first panel located on an upper surface of the housing, the first panel configured to move between an open and a closed position, wherein in a close position, the panel is configured to receive the portable object, and wherein in an open position, the object is configured to be moved into the cavity; a first platform configured inside the cavity, the first platform configured to move the object between a first position and a second position inside the cavity. A plurality of ultraviolet (UV) lights can be positioned at predetermined positions inside the cavity and along a first/upper surface of the first platform. The UV lights are configured to emit UV light of a predetermined wavelength to disinfect the object.

The device further comprises a first driving mechanism operatively coupled to the first panel. The first driving mechanism can be configured to move the first panel between the closed position and the open position. The first driving mechanism further comprises: a set of worm and worm wheel arrangements, configured with the first panel; and a first motor configured to enable actuation of the set of worm and worm wheel arrangements to facilitate the movement of the first panel between the closed position and the open position.

The device further comprises a second driving mechanism operatively coupled to the first platform. The second driving mechanism can be configured to move the first platform between the first position and the second position. The second driving mechanism further comprises: a set of lead screws extending between the first position and the second position, wherein the first platform is movably coupled to the set of lead screws; and a second motor operatively coupled to the set of lead screws to facilitate the movement of the first platform between the first position and the second position.

The device further comprises a second platform configured between the second position and the outlet, wherein the first platform is configured to transfer the object to the second platform at the second position. The second platform can include a conveyor, and wherein the second driving mechanism comprises a third motor operatively coupled to the conveyor to facilitate movement of the object between the second position and the outlet.

The device further comprises a third driving mechanism operatively coupled to the second platform. The third driving mechanism can be configured to move the object from the second position to the outlet.

The device can further include a heating unit positioned inside the cavity. The heating unit can be configured to provide a gentle heat to the object. The heating unit further comprises: one or more heating elements; and a blower to facilitate flow of heated air from the one or more facilitate heating elements towards the object.

The device can further include a spraying unit. The spraying unit can be configured to spray one or more disinfectants over the object. The one or more disinfectants comprises an aromatic or a non-aromatic sanitizer. The device can further include a mechanism for scraping/removing any excess disinfectants.

The device further comprises a computing unit operatively coupled to at least one of: the UV lights, the first driving mechanism, the second driving mechanism, the third driving mechanism, the heating unit, and the spraying unit. The computing unit can be configured to generate a set of control signals to control one or more operations of the device.

The device further comprises a communication unit operatively coupled to the computing unit. The communication unit can be configured to facilitate communication between the device and one or more mobile computing devices.

The device further comprises a payment processing unit operatively coupled to the computing unit. The payment processing unit can be configured to create a secure payment gateway between the device and bank server to facilitate a user in making payment for using the device.

The device further comprises a second panel movably coupled to the outlet. The second panel can be configured to move between a closed position and an open position. The closed position corresponds to a position where the outlet is closed by the second panel, and the open position corresponds to a position where the outlet is open to allow the ejection or removal of the object from the device.

According to an embodiment, a process for disinfecting a portable object involves providing the device discussed herein. The process involves transferring the object from a surface of the device to the first platform; and subjecting the object to UV disinfection inside the device cavity. The process further comprises heating the disinfected object. An aromatic or non-aromatic disinfectant can be further sprayed or spritzed over a surface of the heated object. This is followed by removing the object from the device.

BRIEF DESCRIPTION OF THE DRAWINGS

The accompanying drawings are included to provide a further understanding of the present disclosure and are incorporated in and constitute a part of this specification. The drawings illustrate exemplary embodiments of the present disclosure and, together with the description, serve to explain the principles of the present disclosure.

In the drawings, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION

Figure 1A:
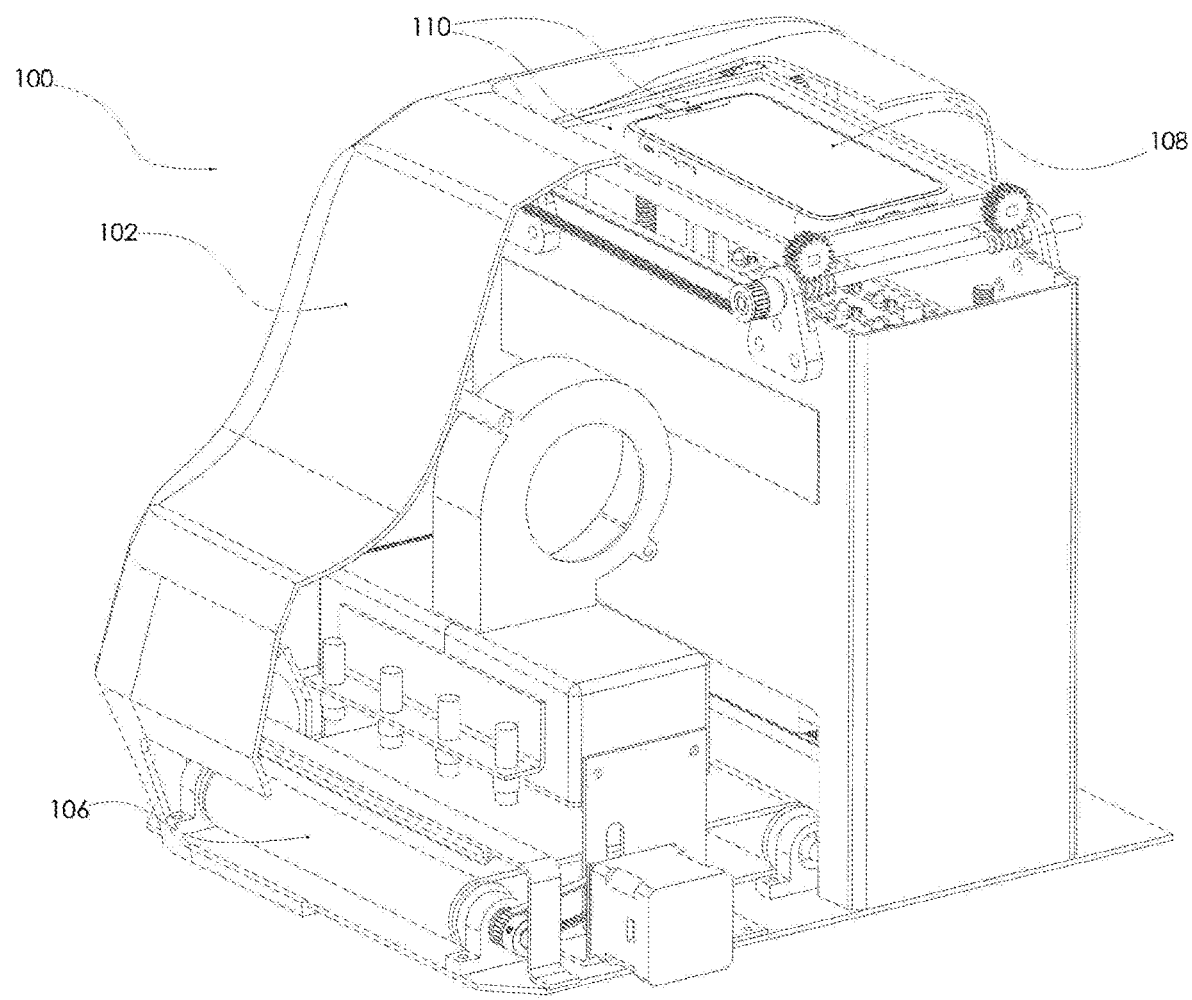
FIGS. 1A to 1C illustrate exemplary views of the device according to an embodiment of the invention.

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Various terms are used herein. To the extent a term used in a claim is not defined below, it should be given the broadest definition persons in the pertinent art have given that term as reflected in printed publications and issued patents at the time of filing.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all groups used in the appended claims.

Embodiments of the present invention include various steps, which will be described below. The steps may be performed by hardware components or may be embodied in machine-executable instructions, which may be used to cause a general-purpose or special-purpose processor programmed with the instructions to perform the steps. Alternatively, steps may be performed by a combination of hardware, software, firmware and/or by human operators.

Embodiments of the present invention may be provided as a computer program product, which may include a machine-readable storage medium tangibly embodying thereon instructions, which may be used to program a computer (or other electronic devices) to perform a process. The machine-readable medium may include, but is not limited to, fixed (hard) drives, magnetic tape, floppy diskettes, optical disks, compact disc read-only memories (CD-ROMs), and magneto-optical disks, semiconductor memories, such as ROMs, PROMs, random access memories (RAMs), programmable read-only memories (PROMs), erasable PROMs (EPROMs), electrically erasable PROMs (EEPROMs), flash memory, magnetic or optical cards, or other type of media/machine-readable medium suitable for storing electronic instructions (e.g., computer programming code, such as software or firmware).

Various methods described herein may be practiced by combining one or more machine-readable storage media containing the code according to the present invention with appropriate standard computer hardware to execute the code contained therein. An apparatus for practicing various embodiments of the present invention may involve one or more computers (or one or more processors within a single computer) and storage systems containing or having network access to computer program(s) coded in accordance with various methods described herein, and the method steps of the invention could be accomplished by modules, routines, subroutines, or subparts of a computer program product.

In the specification, reference may be made to the spatial relationships between various components and to the spatial orientation of various aspects of components as the devices are depicted in the attached drawings. However, as will be recognized by those skilled in the art after a complete reading of the present application, the devices, members, devices, etc. described herein may be positioned in any desired orientation. Thus, the use of terms such as "above," "below," "upper," "lower," "first", "second" or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Figure 1B:
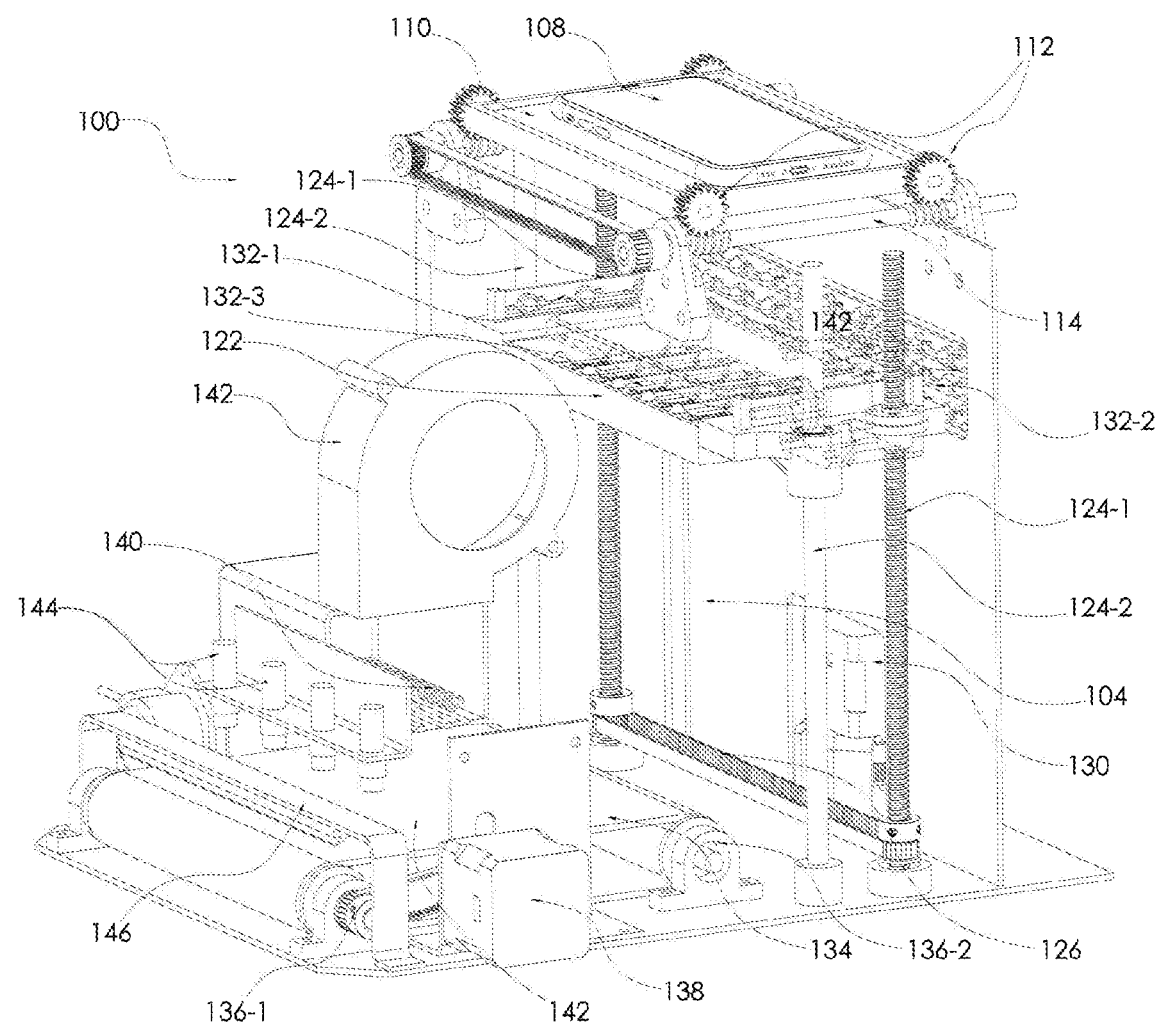
Figure 1C:
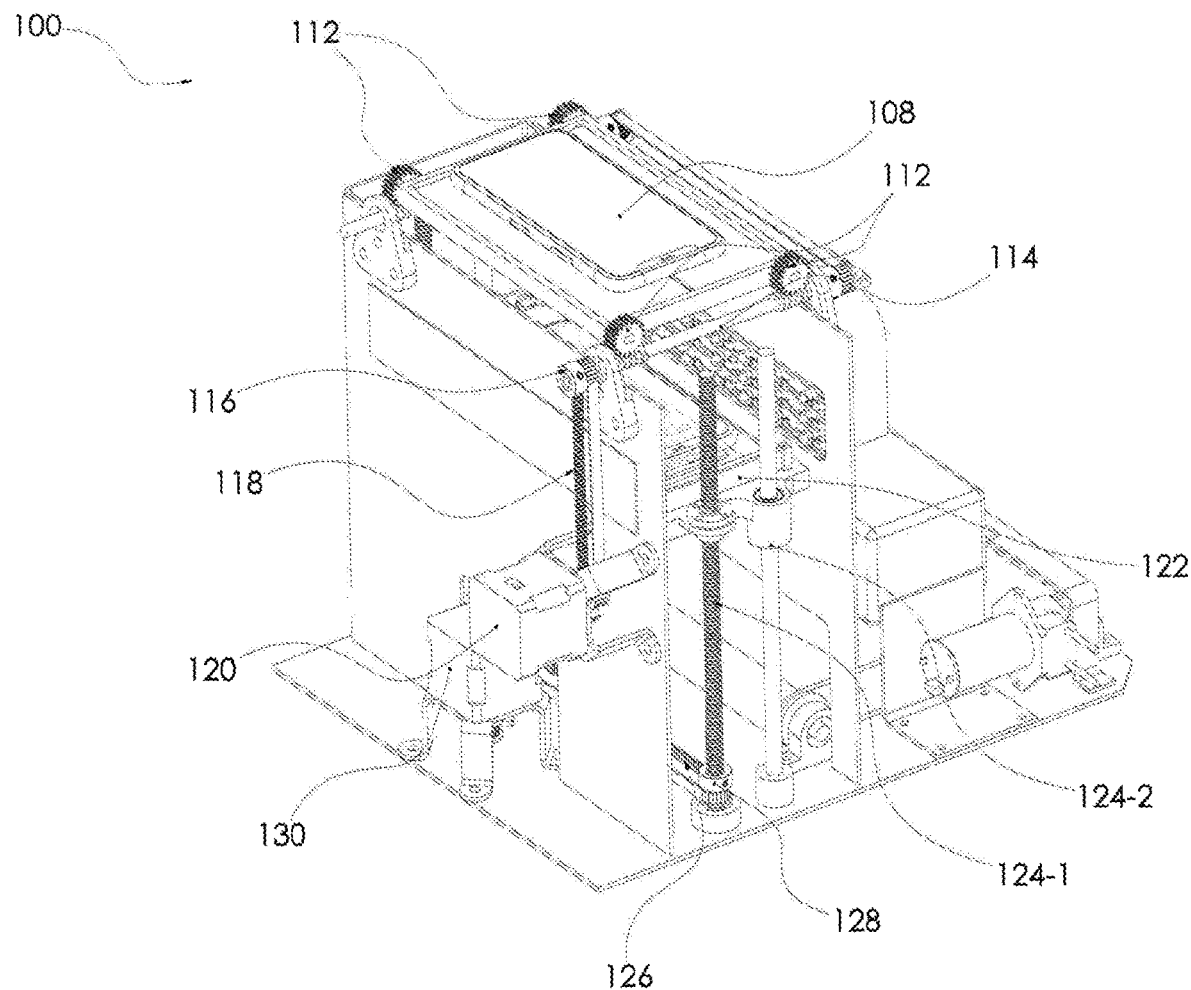

FIGS. 1A to 1C illustrates exemplary views of a device for disinfecting a portable object/object. The device 100 can include a housing 102. The housing 102 can include top and base surfaces, front and rear surfaces, and side surfaces. The housing 102 encloses an internal cavity 104. The housing 102 can be configured to allow placement of the object 108 on an upper surface of the housing 102. The object 108 can be transferred from the upper surface of the housing to the cavity 104 where it is subjected to disinfection. The disinfected object 108 is configured to be removed from an outlet 106.

In an embodiment, the device 100 can include a first panel 110 (also referred to as an inlet door 110 or an inlet flap door 110, herein). The first panel 110 is configured to be movably coupled at an inlet to the cavity 104. In an exemplary embodiment, the first panel 110 can be hingedly coupled to the inlet. In another exemplary embodiment, the first panel can be slidably coupled to the inlet such that the first panel 110 can slide over the inlet, to facilitate opening or closing of the inlet.

The first panel 110 can include, without limitation, a single panel or a set of panels. The first panel 110 can be configured to open and close the inlet. In an embodiment, the first panel 110 can be configured to move between a closed position and an open position. The closed position can correspond to a position where the inlet is closed by the first panel 110, and the open position can correspond to a position where the inlet is at least partially open to facilitate movement of the object 108 into the cavity 104. In the closed position, the object 108 is placed over the top or an upper surface of the first panel 110. When the first panel 110 is moved to the open position, the object 108 can move inside the cavity 104 in a controlled manner.

In an embodiment, the device 100 can include a first driving mechanism (also referred to as inlet closure mechanism, herein) operatively coupled to the first panel 110, and configured to move the first panel 110 between the closed position and the open position. The first driving mechanism can include a set of worm and worm wheels arrangements (112, 114), configured with the first panel 110. However, any other suitable mechanism for opening and closing the first panel can be used.

The first driving mechanism can further include a first motor 120 operatively coupled to the set of worm and worm wheels (112, 114), and configured to enable actuation of the set of worm and worm wheels (112, 114) to facilitate the movement of the first panel 110 between the closed position and the open position. As illustrated, two worm wheels 112 can be coupled to both ends of each of the first panel 110. Further, one threaded worm screw 114 can be rotatably coupled with each of the two worm wheels 112 on both ends of the first panel 110. The first motor 120 can be configured with the threaded worm screw 114 by a set of gears 116, and another set of worm screw 118, such that rotation of the first motor 120 enables rotation of the threaded worm 114 to facilitate rotation of the two worm wheels 112, thereby enabling movement of the first panel 110 between the open position and the closed position.

The device 100 can include a first platform 122 (also referred to as holder 122, herein) for receiving the object from the surface of the first panel. The first platform 122 is located inside the cavity 104 and positioned beneath the inlet and underneath the first panel 110. The first platform 122 can be configured to move between a first position and a second position inside the cavity 104. The first position can correspond to a position where the first platform 122 receives the object 108 when the first panel 110 is in an open position to define an inlet for the object 108. The first position is substantially proximal to the first panel 110. The second position can be at a predefined distance below the first position. The second position can be substantially proximal to a bottom end of the cavity 104. Thus, the first platform 122 can be configured to move between the inlet to the cavity 104 and the bottom end of the cavity 104. In use, the object 108 can be positioned over the first panel 110 when in the closed position. Further, when the first panel 110 is moved to the open position, the object 108 can be moved to the first platform 122 in a controller manner. Once the object 108 is positioned on the first platform 122, the object 108 and the first platform 122 can move towards the second position. In one or more embodiments, the object 108 can be securely clamped to the first platform 122 using a clamping mechanism.

In an embodiment, the device 100 can further include a second driving mechanism (also referred to as sliding mechanism or holder driving mechanism, herein) operatively coupled to the first platform 122. The second driving mechanism can be configured to move the first platform 122 between the first position and the second position. The second driving mechanism can include a set of lead screws 124-1, 124-2 extending between the first position and the second position, along both sides of the first platform 122. Two opposite ends of the first platform 122 can be movably coupled to the set of lead screws 124-1, 124-2. Further, the set of lead screws 124-1, 124-2 can be rotatably coupled to a second motor 130 using a set of gears 126 and another set of lead screws 128. However, other coupling mechanisms can also be used. The second motor 130 is configured to enable rotation of the set of lead screws 124-1, 124-2 thereby facilitating movement of the first platform 122 between the first position and the second position (that is, between the inlet and the bottom end of the cavity 104). In an exemplary embodiment, one of the lead screws 124-1 can be threaded. The lead screws can have the same thread length. Alternately, one of the lead screws, such as, screw 124-2 can have more thread length than the other 124-1.

In another embodiment, the second driving mechanism can include guide rails extending between the first position and the second position, along both sides of the first platform. Further, the two opposite ends of the first platform can be slidably coupled to the guide rails.

The device 100 can include a plurality of ultraviolet (UV) lights 132-1 to 132-3 (collectively referred to as UV lights 132, herein). The UV lights are positioned at predefined/predetermined positions inside the cavity 104, between the first position and the second position. The predefined positions are selected such that an upper and side surfaces of the object 108 are subjected to UV light. Furthermore, the UV lights are also configured along an upper/top surface of the first platform 122 such that the base of the object 108 is also subjected to UV light. In this manner, all surfaces of the object 108 can be treated with UV light. The UV lights 132 can emit UV-C light of wavelength ranging from 220-280 nanometer to facilitate sterilization of the object 108 while moving through the UV-illuminated cavity 104 between the first position and the second position. This can target the DNA of microorganisms, causing cell death or making reproduction impossible. As a result, substantially all the microorganisms present on the object 108 can be killed.

In an exemplary embodiment, the UV lights 132-1 and 132-2 can be positioned at least on opposing inner sidewalls of the housing 102, facing an area between the first position and the second position. One or more row of UV lights 132-1 and 132-2 can be positioned on the inner sidewalls of the housing 102. Further, UV lights 132-3 can also be positioned over an upper surface of the first platform 122, to facilitate UV based disinfection of the base of the object 108 facing the first platform 122. UV lights 132-3 can be arranged in rows that extend the entire length and width of the first platform 122. In this manner, the object 108 placed on the surface of first platform 122 can be completely illuminated by the UV-C light as it is moved between the inlet and the outlet of the housing. This enables substantially complete disinfection of the object 108. Germicidal UV-C lights 134 are available as tubes, either straight or turned into more compact shapes, which can be transparent.

In an embodiment, a second platform 134 (also referred to as conveyor 134, herein) can be configured between the second position and the outlet 106. The first platform 122 can be configured to transfer the UV disinfected object 108 to the conveyor 134 at the second position. In another embodiment, the second driving mechanism can be configured with a tilting mechanism to facilitate controlled tilting of the first platform 122 at a predefined angle, to enable transfer of the UV disinfected object 108 from the first platform 122 to the conveyor 134 at the second position near the bottom end of the cavity 104. One of the set of lead screws 124-2, which is located towards the conveyor, can be provided with more thread length than the other lead screw 124-1 such that the movement of the first platform 122 towards the second position can cause a side of the first platform 122, which is towards the conveyor 134, to move farther compared to the other side of the first platform 122, thereby enabling the first platform 122 to tilt towards the conveyor 134 and allow movement of the UV disinfected object 108 from the first platform 122 to the conveyor 134.

In an embodiment, the device 100 can include a third driving mechanism including a third motor 138 being operatively coupled to the conveyor 134, to move the conveyor 134 and the UV disinfected object 108 from the second position towards the outlet 106. In an exemplary embodiment, the conveyor 134 can be a belt conveyor configured over a set of wheels 136-2, 136-2. The set of wheels 136-1, 136-2 can be driven by the third motor 138 to allow movement of the UV disinfected object 108 from the second position towards the outlet 106.

In an embodiment, the device 100 can include a heating unit positioned at a second predefined position inside the housing, between the second position and the outlet. The heating unit can be configured to provide a very gentle heat to the UV disinfected object 108. In one or more embodiments, the heating unit can heat the object 108 to a predefined temperature. For example, the predefined temperature can be about 1-20-degree Fahrenheit. The predefined temperature can be set below a permissible heating threshold for the object 108 such that the object is not damaged by the heat. Heat is known to kill microorganisms. Therefore, the heating unit is configured to kill any residual microorganisms that remain on the surface of the object 108 after it is treated with the UV light.

The heating unit can include one or more heating elements 140 configured above the conveyor 134. Further, the heating element 140 can include a blower 142 positioned over the one or more heating elements 140 to facilitate a flow of heated air from the one or more heating elements 140 towards the UV disinfected object 108, thereby further disinfecting the object 108. In an exemplary embodiment, the one or more heating elements 140 can be heating coils.

In an embodiment, the device 100 can further include a spritzing/spraying unit 144 positioned at a fourth predefined position between the heating unit and the outlet 106. The spraying unit 144 can include a container for storing at least one disinfectant. The disinfectant can be an alcohol-based disinfectant. The disinfectant can be configured to kill any residual microorganism on the UV disinfected and heated object 108. In an embodiment, the disinfectant can be an aromatic or non-aromatic fluid. In one or more embodiments, the container can include a perfume in lieu of the disinfectant.

The spraying unit 144 can further include one or more sprayers 144 that are fluidically coupled to the container to spritz or spray the one or more disinfectants on the heated and UV disinfected object 108. The sprayers 144 can include a peristaltic pump (also referred to as sanitizer and aroma peristaltic pump, herein). The sprayers 144 can be configured to spray the disinfectant on the object 108 in short bursts which can be configured to operate on a timed cycle.

The conveyor 134 can move the disinfected object 108 out of the device 100 through the outlet 106. In an exemplary embodiment, the device 100 can include a residual/excess disinfectant remover 146 to remove any excess disinfectant, that was sprayed on the surface the object 108, before it exits from the outlet 106. The residual disinfectant remover 146 can include a scraper, a wiper, a brush, or any suitable mechanism known in the art. The residual disinfectant remover 146 can be positioned between the one or more sprayers 144 and the outlet 106.

In an embodiment, the device 100 can include a second panel (also referred to as a second panel or second flap door, herein). The second panel can be movably coupled to the outlet 106. The second panel can include, without limitation, a single panel or a set of panels. The second panel can be configured to move between a closed position and an open position. The closed position can correspond to a position where the outlet 106 is closed by the second panel, and the open position can correspond to a position where the outlet 106 is open to allow removal of the sanitized and disinfected object from the device 100.

In an embodiment, the second driving mechanism can enable the first platform 122 to again move the UV disinfected object 108 towards the first position (inlet) from the second position (base of the cavity). Further, the first driving mechanism can move the first panel 110 to the open position and can allow the user to remove the disinfected object 108 from the inlet side.

The device 100 can be configured to restrict the operation of the heating unit and spraying unit on any object which is sensitive to heat and fluids (disinfecting sanitizers). For such objects, the device 100 can allow only UV based disinfection of the object using the UV lights 132 and it can directly transfer the UV disinfected to the outlet 106 without heating it or spraying a disinfectant on the object.

In an exemplary embodiment, the device 100 can include a door/panel to facilitate, without limitation, any or a combination of refilling of the disinfectant in the spraying unit, maintenance and cleaning of the device 100, removal of the object 108 from the device 100 at any point of disinfecting process. In another exemplary embodiment, the housing 102 of the device 100 can be made of a material selected from any or a combination of plastic, polymer, metal, and any other suitable material. In yet another exemplary embodiment, at least a section of the housing 102 of the device can be made of a transparent material to allow users to view the disinfecting process being performed on the object 108. Further, the housing 102 can be provided with viewing window to allow users to view the disinfecting process being performed on the object 108.

Figure 2:
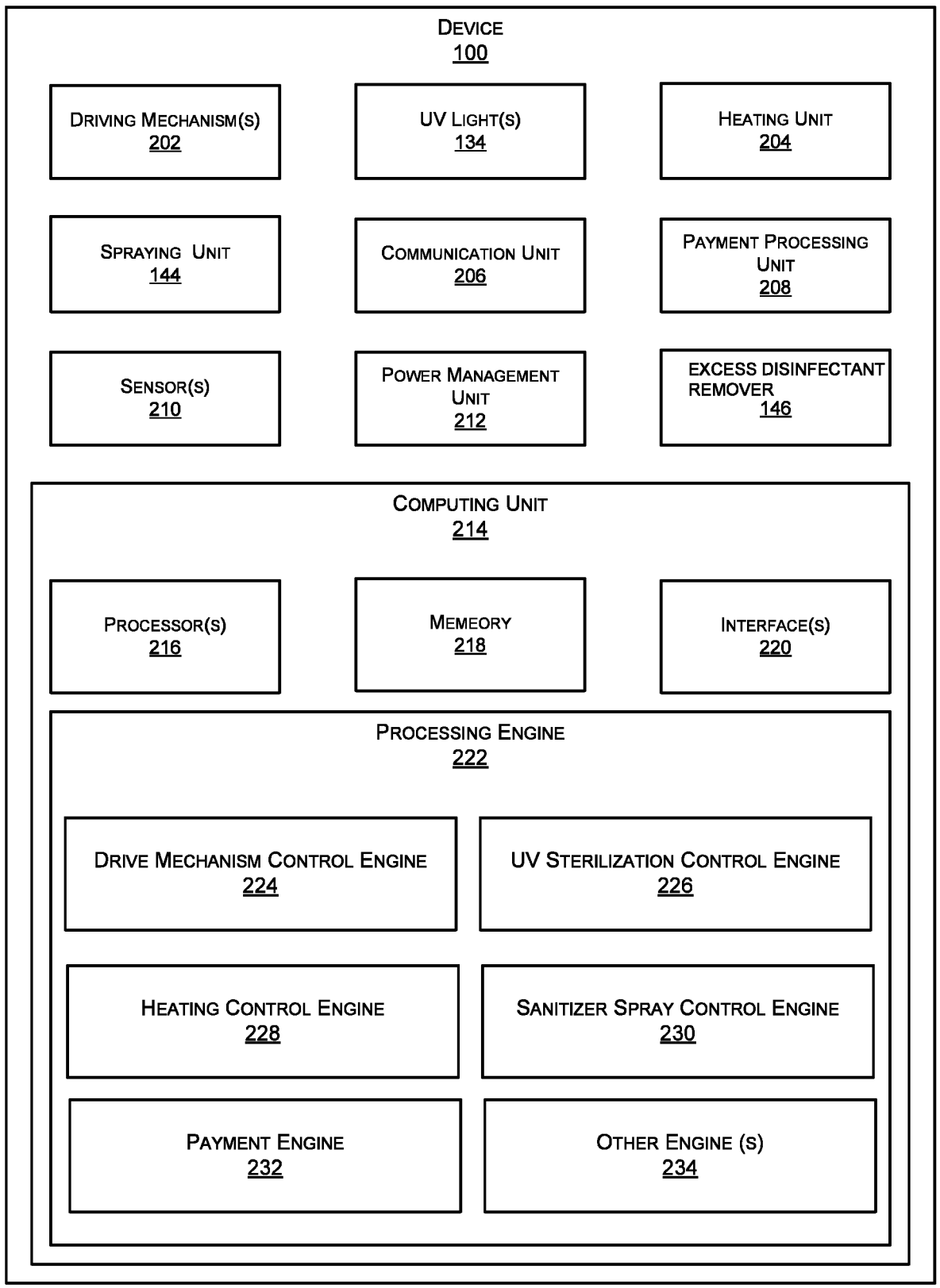
FIG. 2 illustrates a block diagram of the device according to an embodiment of the invention.

FIG. 2 illustrates block diagram of the proposed device, in accordance with an exemplary embodiment of the present disclosure. As illustrated, the device 100 can include driving mechanisms 202 including the first driving mechanism, the second driving mechanism, and the third driving mechanism, to allow controlled movement of the object 108 from the top of the first panel 110 to the outlet 106, through the cavity of the device 100. The device 100 can include the UV lights 132, which can emit UV-C light on the object 108 to disinfect the object 108. The device 100 can include the heating unit 204 to heat the UV disinfected object to further disinfect the object 108. Further, the device 100 can include the sprayers 144 (also referred to as spraying unit 144, herein) to spray a disinfectant (aromatic or non-aromatic) on the heated and UV disinfected object 108, before it exits from the outlet 106 of the device 100.

In an embodiment, the device 100 can include a computing unit 214 operatively coupled to the UV lights 132, the driving mechanisms 202, the heating unit 204, the spraying unit 144 and the residual disinfectant remover 146. The computing unit 214 can be configured to generate a set of control signals to the UV lights 132, the driving mechanisms 202, the heating unit 204, and the spraying unit 144 for controlled operation of the device 100.

In an embodiment, the device 100 can include a communication unit 206 operatively coupled to the computing unit 214, and configured to communicatively couple the device 100 with one or more mobile computing devices (also referred to as mobile devices, herein), such that a user can remotely control the device 100 using the mobile devices. In another embodiment, the device 100 can include a micro-USB connector operatively coupled to the computing unit 214, and it can be configured to operatively couple the device 100 with the mobile devices. The mobile devices can be configured to receive one or more inputs from the user, and correspondingly generate a set of signals. Further, the computing unit 214 can be configured to receive the set of signals from the mobile devices, and correspondingly generate and transmit the set of control signals to any or a combination of the UV lights 132, the driving mechanisms 202, the heating unit 204, and the spraying unit 144 for monitoring and controlled operation of the device.

In an exemplary embodiment, the communication unit 206 can be any or a combination of Bluetooth Module, WiFi Module, Transceivers, and the likes. The mobile devices can be any or a combination of mobile phones, computer, laptop, tablet, and cloud-based server, but not limited to the likes. In another exemplary embodiment, the mobile devices can be Human Machine Interface (HMI) device being coupled with the housing of the device, The HMI can include one or more input means to enable a user to provide one or more inputs to the device 100. The HMI can include a display to provide a visual interface to the user to monitor and control the operations of the device.

In an embodiment, the device 100 can include a payment processing unit 208 operatively coupled to the computing unit 214, and configured to provide a secure payment gateway between the device 100 and bank or a credit card processing server to facilitate the user in making payments for using the device 100.

In an embodiment, the device can include a set of sensors 210 (also referred to as sensors 210, herein) operatively coupled to the computing unit 214 for monitoring one or more parameters associated with the device 100. The one or more parameters can include any or a combination of detecting position and presence of the object 108 at various position inside and outside of the device 100, opening and closing of the panels or doors associated with the inlet and the outlet, and temperature of the object 100 and heating element 140 inside the housing 102. In an embodiment, the sensors 210 can include a first set of sensors. The first set of sensors can be positioned at the inlet and the first platform 122 to detect presence of the object 108 on an upper surface of the first panel 110, and over the first platform 122, respectively. Further, the first set of sensors can detect movement of the first platform 122 and the conveyor 134. In an exemplary embodiment, the first set of sensors can include, without limitation, an infrared sensor and other suitable sensors.

In an embodiment, the sensors 210 can include a second set of sensors, which can be positioned at the inlet and the outlet, and can be configured to detect the opening and closing of the first panel 110 and the second panel at the inlet and the outlet 106, respectively. In an exemplary embodiment, the second set of sensors can include, without limitation, a limit switch.

In an embodiment, the sensors 210 can include a third set of sensors, which can be positioned at any or a combination of the heating unit 204 and the conveyor 134, to monitor the temperature of the object 108 during the disinfecting process. The temperature sensor can include, without limitation, thermistors and other suitable sensors.

In an embodiment, the device 100 can include a power management unit 212 operatively coupled to the computing unit 214, and configured to receive electrical power from one or more power sources, and control the supply of the received electrical power to each component of the device 100. In an exemplary embodiment, the one or more power sources can include, without limitation, a battery, AC mains, and DC power supply.

In an embodiment, the computing unit 214 can include one or more processor(s) 216. The one or more processor(s) 216 can be implemented as one or more microprocessors, microcomputers, microcontrollers, digital signal processors, central processing units, logic circuitries, and/or any devices that manipulate data based on operational instructions. Among other capabilities, the one or more processor(s) 216 can be configured to fetch and execute computer-readable instructions stored in a memory 218 of the device. The memory 218 can store one or more computer-readable instructions or routines, which may be fetched and executed to create or share the data units over a network service. The memory 218 can include any non-transitory storage device including, for example, volatile memory such as RAM, or non-volatile memory such as EPROM, flash memory, and the like.

In an embodiment, the computing unit 214 can also include an interface(s) 220. The interface(s) 220 can include a variety of interfaces, for example, interfaces for data input and output devices, referred to as I/O devices, storage devices, and the like. The interface(s) 220 can facilitate communication of the computing unit with various mobile devices coupled to the device. The interface(s) 220 can also provide a communication pathway for one or more components or modules of the computing unit 214. Examples of such components include, but are not limited to, processing engine(s) 222 and data.

In an embodiment, the processing engine(s) 222 can be implemented as a combination of hardware and programming (for example, programmable instructions) to implement one or more functionalities of the processing engine(s) 222. In examples described herein, such combinations of hardware and programming may be implemented in several different ways. For example, the programming for the processing engine(s) 222 can be processor-executable instructions stored on a non-transitory machine-readable storage medium and the hardware for the processing engine(s) 222 may include a processing resource (for example, one or more processors), to execute such instructions. In the present examples, the machine-readable storage medium may store instructions that, when executed by the processing resource, implement the processing engine(s). In such examples, the computing unit can include the machine-readable storage medium storing the instructions and the processing resource to execute the instructions, or the machine-readable storage medium may be separate but accessible to computing unit and the processing resource. In other examples, the processing engine(s) 222 can be implemented by electronic circuitry. The data can include data that is either stored or generated as a result of functionalities implemented by any of the components of the processing engine(s).

In an embodiment, the processing engine(s) 222 can include a drive mechanism control engine 224, an UV sterilization control engine 226, a heating control engine 228, a disinfectant spray control engine 230, a payment engine 232, and other engine(s) 234. The other engines(s) 234 can implement functionalities that supplement applications or functions performed by the computing unit 214 or the processing engine(s) 222.

In an embodiment, the drive mechanism control engine 224 can enable the computing unit 214 to receive a set of first signals from the mobile devices (where the first set of signals can pertain to controlled operation of the driving mechanisms), and correspondingly generate and transmit a set of first control signals to the any or a combination of the driving mechanisms 202, to allow controlled movement of the object 108 from the upper surface of the first panel 110 to the outlet 106, through the device 100.

In an embodiment, the UV sterilization control engine 226 can enable the computing unit 214 to receive a set of second signals from the mobile devices (where the first set of signals can pertain to controlled UV sterilization or disinfection of the object), and correspondingly generate and transmit a set of second control signals to the UV lights 132 for emitting UV-C light of predefined wavelength on the object 108 while moving along with the first platform 122 between the inlet (first position) and bottom of the cavity (second position).

In an embodiment, the heating control engine 228 can enable the computing unit 214 to receive a set of third signals from the mobile devices (where the set of third signals can pertain to controlled heating of the object by the heating unit), and correspondingly generate and transmit a set of third control signals to the blower 144 and the heating elements 142 of the heating unit 204 for heating the UV disinfected object 108 at the predefined temperature while moving over the conveyor 134, between the second position and the outlet 106.

In an embodiment, the sanitizer spray control engine 230 can enable the computing unit 214 to receive a set of fourth signals from the mobile devices (where the set of fourth signals can pertain to controlled sanitizer spraying of the object by the sprayers 144), and correspondingly generate and transmit a set of fourth control signals to the spraying unit 144 for spraying aromatic sanitizer on the heated object 108 while moving over the conveyor 134, between the second position and the outlet 106

In an embodiment, the payment engine 232 can enable the computing unit 214 to receive a set of fifth signals from the mobile devices (where the set of fifth signals can pertain to payment initiation and payment request by the user for using the device 100), and correspondingly generate and transmit a set of fifth control signals to the payment processing unit 208 to create a payment gateway between the device 100 and bank server to allow the user to make payment for using the device 100.

In an embodiment, the other engines 234 can enable the computing unit to receive a set of sixth signals from the sensors, the set of sixth signals can pertain to the one or more parameters sensed by the sensors 210, including, without any limitation, any or a combination of detecting position and presence of the object 108 at various position inside and outside of the device 100, opening and closing of the panels associated with the inlet and the outlet, and temperature of the object 108 and heating element 140 inside the device 100.

Figure 3:
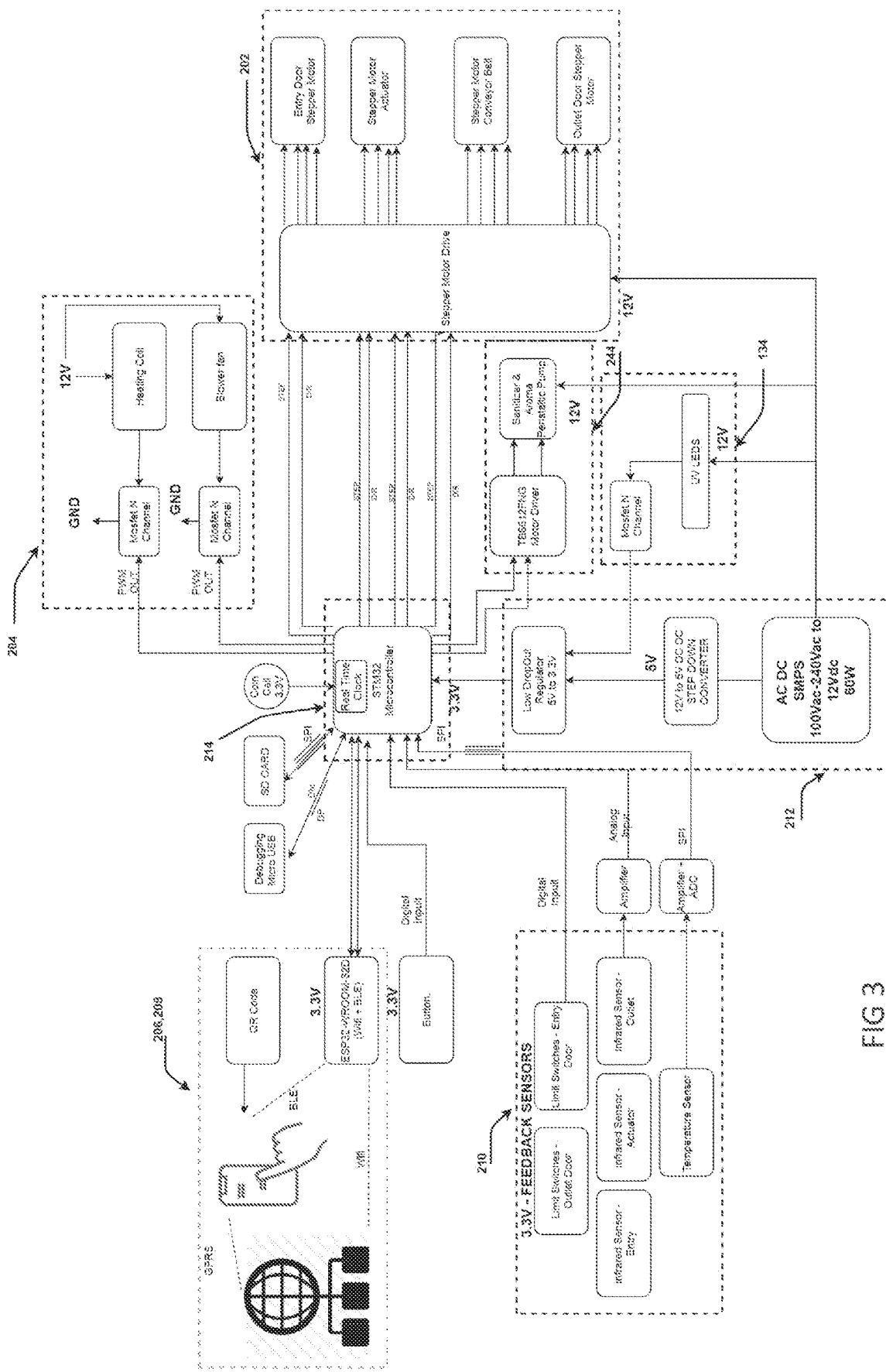
FIG. 3 illustrates an exemplary hardware block diagram of the device according to an embodiment of the invention.

FIG. 3 illustrates an exemplary hardware block diagram of the proposed device, in accordance with an exemplary embodiment. As illustrated, the computing unit 214 of the device 100 can include a Microcontroller STM 32 including a real-time clock, and a memory which can be a SD card, but not limited to the likes. The UV lights 132 can be UV LEDs, being operatively coupled to the Microcontroller by MOSFET N Channel, to emit UV-C light of wavelength 220-280 nm. In an exemplary embodiment, the UV LEDs can require 12 V DC electrical power to operate and emit UV-C light on the object 108 to be disinfected.

In an embodiment, the driving mechanisms 202 of the device 100 can include a stepper motor drive configured with the Microcontroller to operatively couple any or a combination of the first motor 120 associated with the first panel 110 of the inlet, the second motor 130 associated with the first platform 122, the third motor 138 associated with the conveyor 134, and the fourth motor associated with the second panel of the outlet, with the Microcontroller. The Microcontroller can enable the corresponding motors to allow controlled movement of the object 108 from the upper surface of the first panel 110 to the outlet 106, through the device 100. In an exemplary embodiment, the motors associated with the device 100 can be stepper motor that require 12V DC electrical power to operate and enable movement of the object 108 though the device 100.

In an embodiment, the heating coil 140 and the blower 142 can be operatively coupled to the Microcontroller through MOSFET N channels. In an exemplary embodiment, the heating coil 140 and the blower 142 can require 12V DC electrical power to operate and provide the predefined temperature to the object 108 to be disinfected.

In an embodiment, the device 100 can include a TB6612FNG motor drive operatively coupled between the Microcontroller and the sanitizer and peristaltic pump of the spraying unit 144 to dispense or spray the aromatic/non-aromatic disinfectant on the object 108 before exiting from the outlet of the device 100. The sanitizer and peristaltic pump can operate on 12V DC power.

In an embodiment, the device 100 can include one or more buttons operatively coupled to the Microcontroller to facilitate the user to feed one or more inputs in the device 100 to control the device and the disinfection process. The actuation or pressing of the one or more buttons based on the one or more inputs, can generate and transmit the set of control signals to the Microcontroller.

In an embodiment, the device 100 can include the sensors 210 being operatively coupled to the Microcontroller for monitoring one or more parameters associated with the device 100. The one or more parameters can include any or a combination of detecting position and presence of the object 108 at various position inside and outside of the device 100, opening and closing of the panels associated with the inlet and the outlet, and temperature of the object 108 and heating coil 140 inside the device 100. The sensors 210 can monitor the one or more parameters, and correspondingly generate the set of signals, which can be amplified by amplifiers and converted into digital signals, and transmit the amplified digital signal to the Microcontroller.

In an embodiment, the sensors 210 can include a first set of sensors (such as, infrared or IR sensors), each positioned at the inlet and the first platform 122 to detect presence of the object 108 at the upper surface of the first panel 110, and over the first platform 122, respectively. Further, the IR sensors can detect movement of the first platform 122 and the conveyor 134. In another embodiment, the sensors 210 can include a second set of sensors (such as, a limit switch), each positioned at the inlet and the outlet 106, and configured to detect opening and closing of the first panel 110 and the second panel at the inlet and the outlet, respectively. In yet another embodiment, the sensors 210 can include a third set of sensors, each positioned at any or a combination of the heating unit 204 and the conveyor 134, to monitor temperature of the object 108 during disinfecting process.

In an embodiment, the power management unit 212 of the device 100 can be operatively coupled to the Microcontroller. The power management unit 212 can include an AC-DC SMPS of rating 100 Vac-240ac to 12 VDc, 60 W, to convert AC voltage ranging from 100V to 204V, into 12V DC. The AC-DC SMPS can be configured to receive electrical power from one or more power sources, and control the supply of the received electrical power to each component of the device 100. In an exemplary embodiment, the one or more power sources can be battery, AC mains, and DC power supply, but not limited to the likes. The AC-DC SMPS can directly supply 12V DC power to the UV LEDs, the stepper motor drive, and the sanitizer and aroma peristaltic pump. The power management unit 212 can include a 12V to 5V DC-DC step down converter and a low drop out 5V to 3.3 V regulator, being operatively coupled between the AC-DC SMPS and the Microcontroller, to supply 3.3V DC power to the Microcontroller.

In an embodiment, the communication unit 206 of the device 100 can be ESP32-WROOM-35 WIFI-Bluetooth module, being operatively coupled to the Microcontroller, and configured to communicatively couple the proposed device 100 with the mobile devices 100. The device 100 can include a Micro USB connector operatively coupled to the Microcontroller, and configured to operatively couple the proposed device 100 with the mobile devices 100. In another embodiment, the ESP32-WROOM-35 WIFI-Bluetooth module, can be configured to communicatively couple the payment processing unit 208 of the device 100 with the mobile devices 100 associated with bank server, to provide a secure payment channel between the mobile devices 100 associated with user of the device 100 and the bank server. In an exemplary embodiment, the payment processing unit 208 can enable the user to make payment for using the device 100 by scanning a QR code and/or by using a mobile-based application installed on the mobile computing device 100 of the user.

Figure 4A:
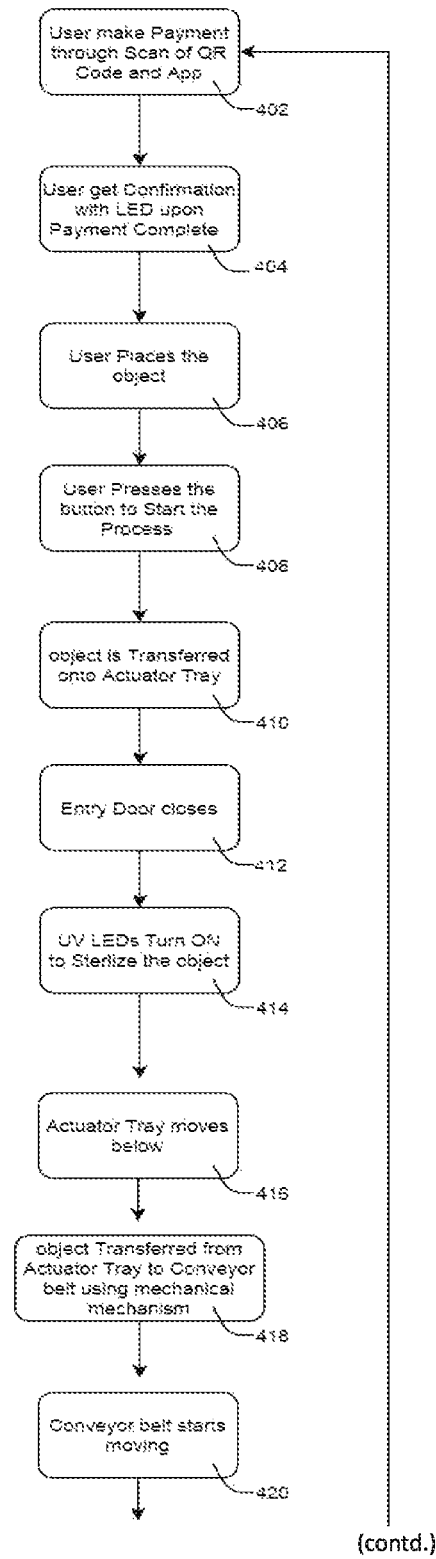
FIG. 4A illustrates an exemplary method of using the device according to an embodiment of the invention.

FIG. 4A illustrates an exemplary process flow diagram for disinfecting an object using the device 100. The process of disinfecting the object 100 can include a step 402 of making payment for using the device 100, using a mobile device associated with the user, either by scanning a QR code associated with the proposed device or by a mobile-based application being installed on the mobile devices of the user.

The process can include a step 404 of receiving payment confirmation after the payment step 402. Upon confirmation of the payment, the device 100 can generate an indication for payment confirmation using one or more LEDs or alarms, and can allow the user to commence use the device 100.

The process can further include a step 406 of placing the object 100 to be disinfected on an upper surface of the closed first panel 110, upon payment confirmation in step 404. The process can further include a step 408 of pressing or actuating the buttons associated with the device, to initiate the disinfection process on the object 108.

At step 410, object is moved by the opening of the first panel 110 to the first platform 122, followed by a step 412 of closing the inlet by the first panel 110.

At step 414, the process involves enabling the UV lights 132, by the Microcontroller, to emit UV-C light on the object 108 to facilitate disinfection of the object 108. The process can further include a step 416 of moving the first platform 122 from the first position to the second position in the UV illuminated cavity 104.

The process can further include a step 418 of transferring the UV disinfected object 108 from the first platform 122 to the conveyor 134 at the second position.

At step 420, the object 108 is moved over the conveyor 134, between the second position and the outlet 106.

At step 422, the object 108 can be subjected to heating by the heating unit by blowing heated air over the object.

In step 424, the object 108 is moved below the spraying unit, to spray a disinfectant over the object 108.

The process can further include a step 426 of moving the second panel associated with the outlet 106 to open the outlet 106, followed by a step 428 to allow exiting of the disinfected object 108. Further, upon exiting of the object from the device 100, the process can include a step 430 of moving the second panel associated with the outlet 106 to close the outlet 106.

In an embodiment, upon successful disinfection and removal of the object 108 from the outlet 106 in a step 432, the process can again move to the step 402 of allowing a user to make payment for using the device 100.

FIG. 4B to 4G illustrate exemplary views of the proposed device during various stages of disinfection and sterilization of the object by the device, in accordance with an exemplary embodiment, to elaborate upon the working of the device.

Figure 4B:
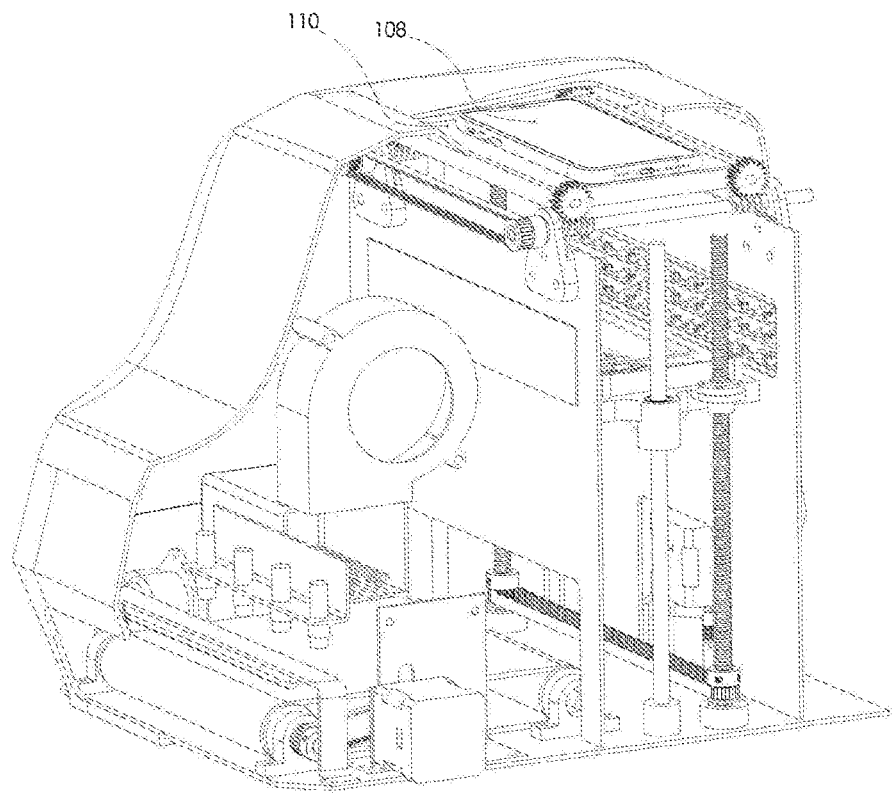
FIGS. 4B to 4G illustrate exemplary views of the device according to an embodiment of the invention.

As illustrated in FIG. 4B, in an embodiment, the process can further include a step of placing the object 100 to be disinfected on the upper surface of the closed first panel 110, upon payment confirmation by the payment processing unit 208 of the device. The payment processing unit 208 and the communication unit 206 can facilitate creating a secure payment channel between the proposed device 100 as well as the mobile devices of the user, and the bank server. The IR sensor positioned at the first panel 110, can detect presence of the object 108 on the first panel 110. Further, upon, detection of the object 108 on the upper surface of the first panel 110, the device 100 can generate indication for initiating the disinfecting process, using the one or more LEDs. The process can further include a step of pressing or actuating the buttons associated with the device, to initiate the disinfection process on the object 108.

Figure 4C:
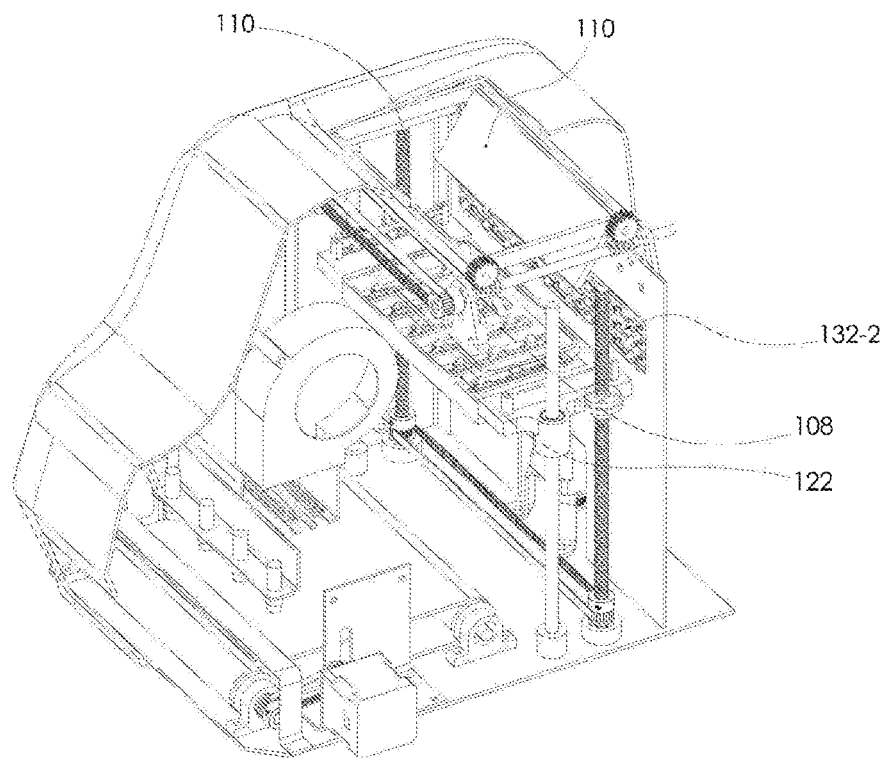

As illustrated in FIG. 4C, in an embodiment, the process can further include a step of moving the first panel 110, by the first driving mechanism, to the open position, to facilitate movement of the object 108 from the upper surface of the first panel 110 to the first platform 122. The Microcontroller can enable the first driving mechanism to move the first panel 110 from the closed position to the open position. Once, the IR sensor associated with the first platform 122 and the first panel 110 confirms that the object 108 has been transferred onto the first platform 122, the first driving mechanism moves the first panel 110 to the closed position, thereby closing the inlet. Further, the limit switch associated with the first panel 110 can facilitate the Microcontroller to confirm if the inlet is completely closed.

Figure 4D:
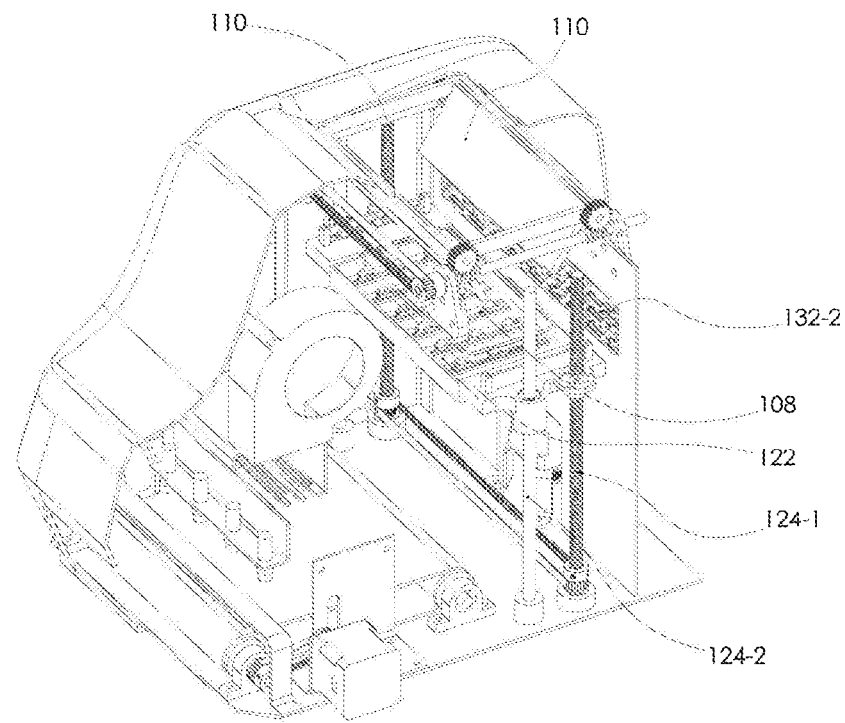

As illustrated in FIG. 4D, in an embodiment, the process can include a step of enabling the UV lights 132, by the Microcontroller, to emit UV-C light on the object 108 to facilitate disinfection of the object 108. The Microcontroller can enable the second driving mechanism to move the object 108 from the first position to the second position at a predefined speed, through the UV illuminated cavity 104. Further, the IR sensor associated with the first platform 122 can monitor the movement of the object 108 and the first platform 122 in the cavity 104.

Figure 4E:
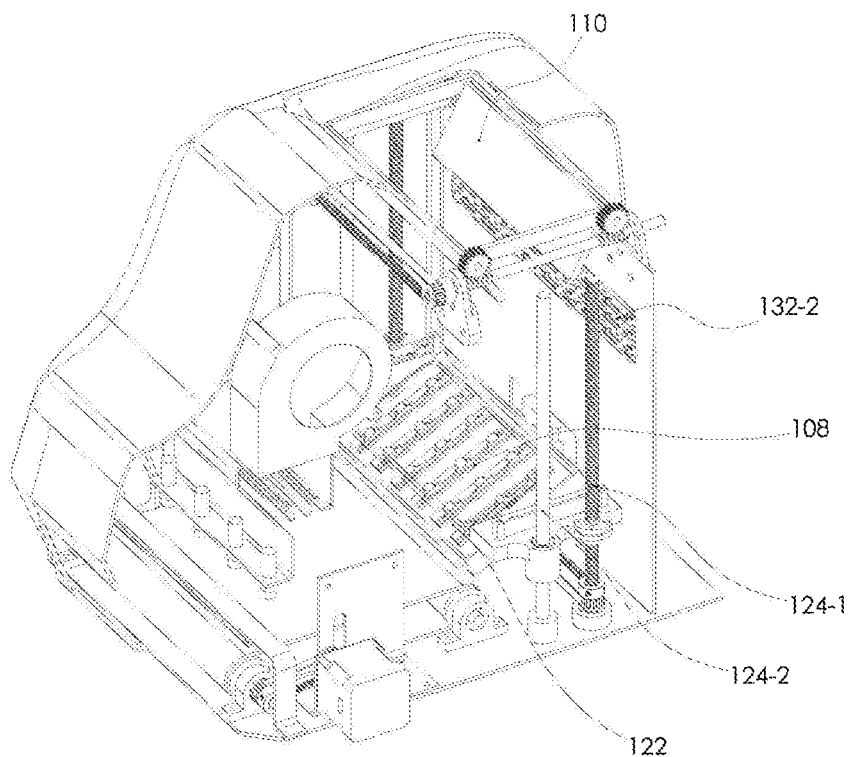

As illustrated in FIG. 4E, in an embodiment, the process can further include a step of transferring the UV disinfected object 108 from the first platform 122 to the conveyor 134 at the second position. The tilting mechanism configured with the first platform 122 and the second driving mechanism can tilt the first platform 122 by the predefined angle to transfer the object 108 to the conveyor 134. The IR sensor associated with the first platform 122 and the conveyor 134 can monitor the movement of the object 108 and can facilitate the Microcontroller to confirm if the object 108 is completely transferred onto the conveyor.

Figure 4F:
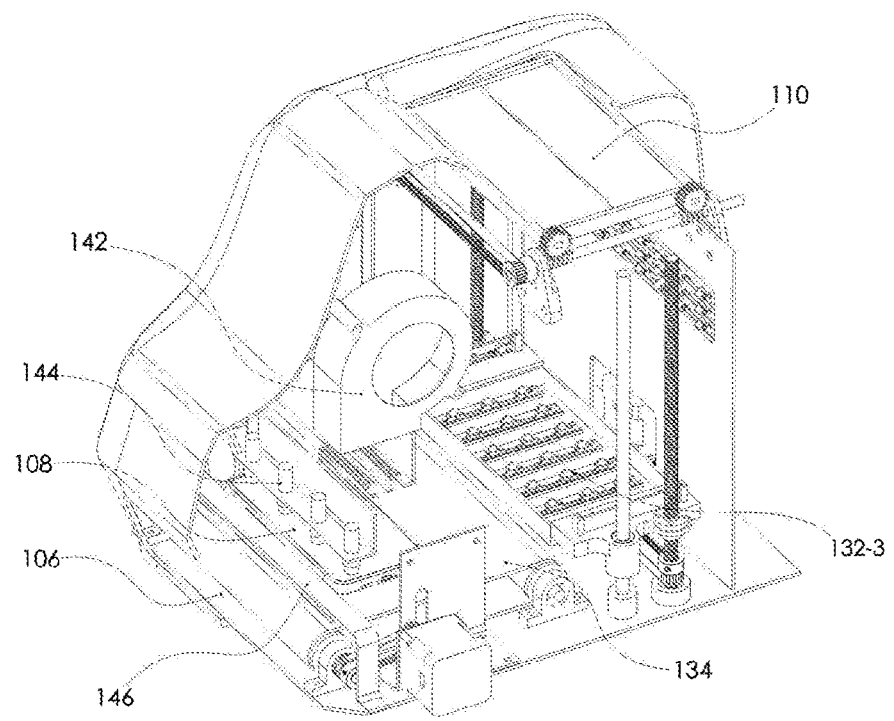

As illustrated in FIG. 4F, in an embodiment, the process can include a step of driving the conveyor 134, by the third driving mechanism, once the Microcontroller gets confirmation that the object 108 has been completely transferred on the conveyor 134. The Microcontroller can enable the third driving mechanism and the conveyor 134 to move the object 108 over the conveyor 134 from the second position to the outlet 106 of the device 100.

In an embodiment, the Microcontroller can enable the heating unit 204 to blow heated air at the predefined temperature, towards the object 108 moving over the conveyor 134. The Microcontroller can enable the heating elements 140 to get heated, and can further enable the blower 142 to blow air towards the heating elements 140 such that the heated air blows towards the object 108.

In an embodiment, the Microcontroller can enable the spraying unit 144 to spray a disinfectant on the object 108 moving over the conveyor. The Microcontroller can enable the peristaltic pump to spray or dispense the disinfectant on the object 108. Any residual disinfectant can be removed by the excess disinfectant remover 146 before the object exits the device.

Figure 4G:
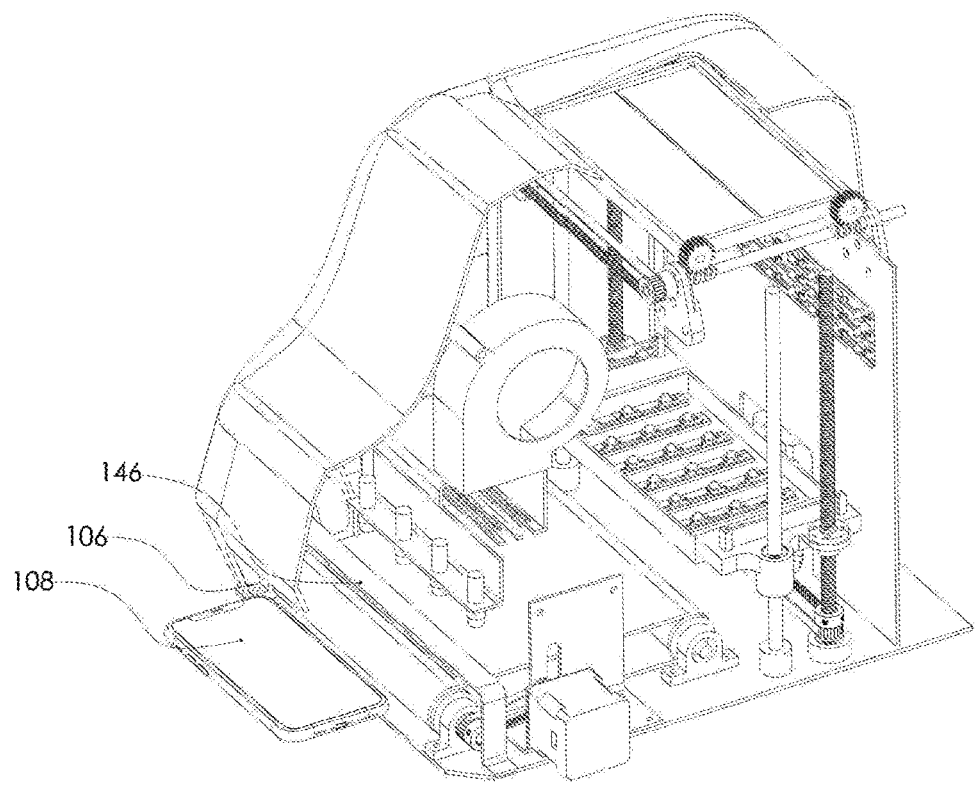

As illustrated in FIG. 4G, in an embodiment, the process can further include a step of moving the second panel associated with the outlet 106 to open the outlet 106 and allow exiting of the disinfected object 108. The limit switch associated with the outlet 106 can detect if the second panel of the outlet 106 are open or not. Once, the limit switch gives confirmation to the Microcontroller that the outlet 106 is open, the Microcontroller can enable the third driving mechanism to facilitate the conveyor 134 in moving the object 108 out of the device 100 through the outlet 106.

In an embodiment, the IR sensor being positioned at the second panel can confirm if the object is completely out of the device. Once, the IR sensor associated with the second panel confirms that the object 108 has been completely moved out of the device 100 through the outlet, the fourth driving mechanism associated with the second panel can move the second panel to the closed position, thereby closing the outlet 106. Further, the limit switch associated with the second panel can facilitate the Microcontroller to confirm if the outlet is closed. Upon confirming that the object 108 is completely out of the device 100 and the second panel are completely closed, the device 100 can generate an indication for process completion, using one or more LEDs, and can allow the user to collect the disinfected object.

While the device does not include any polishing or debris removal mechanisms, it is envisioned that the device 100 of the present invention can be sold as a kit with a package of cleansing/disinfecting wipes, such as, electronic wipes. The device 100 can be configured to disinfect a single portable object at a time.

The disinfection treatment can substantially remove over 90% of the germs and microorganisms on the surface of the portable object.

Therefore, the present invention is well adapted to attain the ends and advantages mentioned as well as those that are inherent therein.

In interpreting the specification, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

The invention claimed is:

1. A device for disinfecting a portable object, the device comprising:
   a housing, the housing comprising an outlet, and wherein the housing encloses a central cavity;
   a first panel located on an upper surface of the housing, the first panel configured to move between an open and a closed position, wherein in the closed position, the first panel is configured to receive the portable object on an upper surface of the first panel, and wherein in the open position, the object is configured to be moved from the upper surface of the first panel into the cavity;
   a first driving mechanism operatively coupled to the first panel, the first driving mechanism configured to move the first panel between the closed position and the open position;
   a first platform configured inside the cavity, the first platform configured to receive the object when the first panel is in the open position, and move between a first position and a second position inside the cavity to facilitate movement of the object between the first position and the second position inside the cavity; and
   a plurality of ultraviolet (UV) lights positioned along an upper surface of the first platform; and
   a plurality of UV lights positioned at predetermined positions inside the cavity,
   wherein the UV lights are configured to emit UV light of a predetermined wavelength to disinfect the object.

2. The device according to claim 1, wherein the first driving mechanism further comprises:
   a set of worm and worm wheel arrangements, configured with the first panel; and
   a first motor configured to enable actuation of the set of worm and worm wheel arrangements to facilitate the movement of the first panel between the closed position and the open position.

3. The device according to claim 1, further comprising a second driving mechanism operatively coupled to the first platform, the second driving mechanism configured to move the first platform between the first position and the second position.

4. The device according to claim 3, wherein the second driving mechanism further comprises:
   a set of lead screws extending between the first position and the second position, wherein the first platform is movably coupled to the set of lead screws; and
   a second motor operatively coupled to the set of lead screws to facilitate the movement of the first platform between the first position and the second position.

5. The device according to claim 1, further comprising a second platform configured between the second position and the outlet, wherein the first platform is configured to transfer the object to the second platform at the second position.

6. The device according to claim 5, wherein the second platform is a conveyor, and wherein the second driving mechanism comprises a third motor operatively coupled to the conveyor to facilitate movement of the object between the second position and the outlet.

7. The device according to claim 5, further comprising a third driving mechanism operatively coupled to the second platform, the third driving mechanism configured to move the object from the second position to the outlet.

8. The device according to claim 7, further comprising a heating unit positioned inside the cavity, and wherein the heating unit is configured to provide a gentle heat to the object.

9. The device according to claim 8, wherein the heating unit further comprises:
   one or more heating elements; and
   a blower to facilitate flow of heated air from the one or more facilitate heating elements towards the object.

10. The device according to claim 8, further comprising a spraying unit, the spraying unit configured to spray a disinfectant over the object.

11. The device according to claim 10, further comprising an excess disinfectant remover to remove excess disinfectant from a surface of the object.

12. The device according to claim 10, further comprising a computing unit operatively coupled to at least one of: the UV lights, the first driving mechanism, the second driving mechanism, the third driving mechanism, the heating unit, and the spraying unit, and wherein the computing unit is configured to generate a set of control signals to control one or more operations of the device.

13. The device according to claim 12, further comprising a communication unit operatively coupled to the computing unit, the communication unit configured to facilitate communication between the device and one or more mobile computing devices.

14. The device according to claim 13, further comprising a payment processing unit operatively coupled to the computing unit, the payment processing unit configured to create a secure payment gateway between the device and bank server to facilitate a user in making payment for using the device.

15. The device according to claim 1, further comprising a second panel movably coupled to the outlet, the second panel configured to move between a closed position and an open position, and wherein the closed position corresponds to a position where the outlet is closed by the second panel, and the open position corresponds to a position where the outlet is open to allow removal of the object.

16. The device according to claim 1, wherein the portable object is a mobile phone.

\* \* \* \* \*